US005569660A

United States Patent [19]

Snowden et al.

[11] Patent Number: 5,569,660

[45] Date of Patent: Oct. 29, 1996

[54] UTILIZATION OF AN ALKYL-SUBSTITUTED PYRIDINE AS A PERFUMING INGREDIENT

[75] Inventors: Roger L. Snowden, Viry, France; Pierre-Alain Blanc, Crassier, Switzerland

[73] Assignee: Firmenich SA, Geneva, Switzerland

[21] Appl. No.: 443,227

[22] Filed: May 17, 1995

[30] Foreign Application Priority Data

Jun. 21, 1994 [CH] Switzerland ............................ 1966/94

[51] Int. Cl.$^6$ .................................................. A61K 31/435

[52] U.S. Cl. ........................... 514/277; 424/65; 424/70.1; 512/1; 512/8; 512/10; 546/348

[58] Field of Search .................................... 514/300, 277; 424/70, 71

[56] References Cited

PUBLICATIONS

E Langhals et al., "A Simple synthesis of 5–cyano–2pyridine carboxylic acid and its amide" Chem. Ber. 117 1259–1261 (1984).

O. Tsuge et al., "Reactions of 1,4–bis(trimethylsilyl)–1, 4–dihydropyridines with carbonyl compounds: a new method for regioselective synthesis of 3=alkyl ptridines" Bull. Chem. Soc. Jpn, 60, 1497–1504 (1987).

O. Tsuge et al., "Regioselective alkyl group introduction at the 3–position of pyridine via of 1,4–bis(trimethylsilyl)–1, 4–dihydropyridine" Chem. Lett. pp. 1255–1258 (1984).

*Primary Examiner*—Shelley A. Dodson
*Attorney, Agent, or Firm*—Pennie & Edmonds

[57] ABSTRACT

3-(2,2-Dimethyl-propyl)-pyridine is used to impart, improve or modify the odor properties of a variety of consumer products. In particular, it develops fruity-fresh type notes.

4 Claims, No Drawings

UTILIZATION OF AN ALKYL-SUBSTITUTED PYRIDINE AS A PERFUMING INGREDIENT

BRIEF SUMMARY OF THE INVENTION

The invention relates to a method to impart, improve, enhance or modify the odor properties of a perfuming composition or of a perfumed article, which method comprises adding to said composition or article a fragrance effective amount of 3-(2,2-dimethyl-propyl)-pyridine.

Another object of the invention is a method to impart, improve, enhance or modify the odor properties of perfumes, colognes, skin or body-care products, cosmetic preparations, body deodorants or air fresheners, shampoos, hair-care products, soaps, detergents, fabric softeners or household products, which consists in adding thereto 3-(2, 2-dimethyl-propyl) -pyridine as a perfuming ingredient.

The invention also relates to the compositions and products resulting from these methods.

BACKGROUND OF THE INVENTION

Pyridine, as well as some of its alkyl derivatives, is known in the flavor industry, namely for reconstituting coffee type aromatic compositions, or even meat type flavors. The situation is quite different in perfumery where the use of pyridines is far less documented.

Pyridine is described by S. Arctander [Perfume and Flavor Chemicals, Montclair, N.J. (USA), 1969, sec. 2776] as possessing an irritant, penetrating and diffusive odor, occasionally defined as disgusting, which, at high dilution, can reveal itself as being warm, burnt and very weakly tenacious.

Certain alkylated pyridines have been identified in natural origin products. Thus n-pentyl-pyridine has been identified in jasmine absolute from Egyptian origin [see Mostafa A. Nofah et al., Perfumer & Flavorist 6,24 (1982)], whereas 2-, 3- and 4-butyl-pyridine are components of spearmint essential oil [T. Tsuneya et al., Bioactive volatile compounds from Plants, ACS Symposium Series 525 (1992)].

Finally, 3-ethyl- and 4-methyl-3-ethyl-pyridine have been identified in jasmine essential oil by T. Toyoda et al. [Proceedings VII th International Essential Oil Congress, Kyoto, p. 473–76 (1979)]. To the best of our knowledge, there has been strictly no mention up to this day of the use of 3-(2,2,-dimethyl-propyl)-pyridine in perfumery, nor indeed of its occurrence in a natural product.

DETAILED DESCRIPTION OF THE INVENTION

We have been able to establish that the compound in question possesses a very pleasant odor character of the fruity type. It develops in particular an agreeable fresh-fruity note, some nuances of which are reminiscent of the typical odor of ripe pear or banana, with a connotation recalling the odor of camomile or caraway. 3-(2,2-Dimethyl-propyl)-pyridine has shown very good tenacity and excellent substantivity on textiles, together with an important odor strength. In practice, it appeared that this compound possessed a fresh and fruity flagrance, which in itself is quite surprising, considering the characters presented by other analogue compounds prior known, which are rather phenolic, pyrogenic and aminelike.

As a result of its odor properties, 3-(2,2-dimethyl-propyl)-pyridine finds wide use in a variety of applications, both in fine and technical perfumery. It can also be used for the total or partial reconstitution of concentrated perfuming bases.

Whether directly added to the products that one desires to perfume or, more currently, in admixture with other common perfuming ingredients, solvents or excipients currently used, 3-(2,2-dimethyl-propyl)pyridine can serve to impart, improve, enhance or modify the characteristic odor properties of consumer products as varied as perfumes, colognes, skin or body-care products, cosmetic preparations, body deodorants or air fresheners, shampoos, hair-care products, soaps, detergents, fabric softeners or yet household products.

Obviously, it can also be used for the preparation of concentrated perfuming bases.

The proportions in which the pyridine in question is employed within the scope of the utilisation defined in the present invention vary in a wide range of values. They can in fact be comprised between 1 and 10% by weight, relative to the weight of the product to which 3-(2,2-dimethylpropyl) -pyridine is added. It goes without saying that such concentration values are not to be construed as being absolute values, the skilled person being quite capable of adapting the proportion of the ingredient in question as a function of the desired fragrance effect, the nature of the products to be perfumed, as well as that of the other co-ingredients possibly present in a given composition.

When perfuming soaps and detergents for example, lower concentrations, of the order of 0.1–0.5% by weight, can be perfectly convenient, whereas concentrations beyond 10% may be necessary for preparing concentrated perfuming bases.

3-(2,2-Dimethyl-propyl)-pyridine is a known chemical, which has been described in the scientific literature namely as a synthesis intermediate or starting product for the preparation of compounds useful for the polymer or pharmaceutical industry.

Several synthetic methods for its preparation have been disclosed, for instance by O. Tsuge et al., Chemistry Letters Japan, 1984, 1255–58; O. Tsuge et al., Bull. Chem. Soc. Japan 60, 1497–1504 (1987) and E. Langhals et al., Chem. Ber. 117, 1259–1261 (1984).

The object of the present invention is therefore the use of 3-(2,2-dimetyl-propyl) -pyridine as a perfuming ingredient.

Likewise, it is another object of the invention to provide a perfuming composition containing as active perfuming ingredient 3-(2,2-dimethyl-propyl) -pyridine.

Other objects of the invention, namely the methods to confer, improve, enhance or modify the odor properties of a variety of consumer products by way of said pyridine, as well as the products thus modified, have already been mentioned above.

The invention is illustrated by means of, but not limited to, the following examples.

EXAMPLE 1

A base perfuming composition having a fruity-pear character was prepared by admixing the following ingredients:

| Ingredients | Parts by weight |
|---|---|
| Hexyl acetate | 10 |
| Linalyl acetate | 100 |
| Terpenyl acetate | 190 |
| TCD acetate[1)] | 100 |

-continued

| Ingredients | Parts by weight |
|---|---|
| Methyl cinnamate | 20 |
| γ-Dodecalactone | 25 |
| 50% [a)]β-Dorinone ®[2)] | 220 |
| 10% [a)]Dynascone ® 10%[a) 3)] | 10 |
| Lilial ®[4)] | 200 |
| 10% [a)]Melonal ®[4) 5)] | 5 |
| Linalyl oxide | 10 |
| Veloutone[6)] | 50 |
| γ-Undecalactone | 50 |
| Total | 990 |

[a)]dipropylene glycol
[1)](tricyclo[5.2.1.0$^{2,6}$]dec-4-yl)methyl acetate
[2)]origin: Firmenich SA, Geneva, Switzerland
[3)]1-(5,5-dimethyl-cyclohex-1-enyl)-pent-4-en-1-one; origin: Firmenich SA, Geneva, Switzerland
[4)]origin: Givaudan-Roure (registered trademark)
[5)]2,6-dimethyl-5-heptenal
[6)]2,2,5-trimethyl-5-pentyl-cyclopentanone; origin: Firmenich SA, Geneva, Switzerland When there is added to 99 parts by weight of the thus prepared base one part of 3-(2,2-dimethyl-propyl)-pyridine, one obtains a novel composition with an enhanced fruity-pear character. Its odor appears as more natural, with a peel nuance. Furthermore, the whole becomes less alimentary juice.

EXAMPLE 2

A base perfuming composition of the tobacco-floral, powdery type, was prepared by admixing the following ingredients:

| Ingredients | Parts by weight |
|---|---|
| Benzyl acetate | 60 |
| Linalyl acetate | 80 |
| Phenylacetic acid | 20 |
| Bergamot essential oil | 180 |
| 10% [a)]Birchwood essential oil | 20 |
| Coumarine | 80 |
| 10% [a)]Damascenone[1)] | 20 |
| Dimethylhydroquinone | 80 |
| 10% [a)]β-Dorinone ®[2)] | 20 |
| Heliotropine | 90 |
| Iralia ®[3)] | 90 |
| 10% [a)]α-Irone | 20 |
| Linalol BJ | 60 |
| Myrrh essential oil | 70 |
| Methyl phenylacetate | 20 |
| Phenylethyl phenylacetate | 20 |
| Tonalid ®[4)] | 30 |
| Total | 960 |

[a)]dipropylene glycol
[1), 2)]origin: Firmenich SA, Geneva, Switzerland
[3)]methylionone; origin: Firmenich SA, Geneva, Switzerland
[4)]origin: Polak's Frutal Works (registered trademark)

When one adds to 96 parts by weight of the base composition above 4 parts by weight of 3-(2,2-dimethyl-propyl)-pyridine, there is obtained a novel composition having an elegant character and whose typical note resulting from the presence of phenylacetic acid was distinctly improved. The character of the ensemble also becomes more natural and floral, as well as less animal and more fruity-sweet.

The 3-(2,2-dimethyl-propyl)-pyridine used in the preceding examples showed the following analytical characters:

B. p. 80–83°/1.33x$10^3$ Pa IR($CHCl_3$): 2961, 1577, 1478, 1424, 1366, 1238 and 1192 $cm^{-1}$ NMR($^1H$): 0.92(s, 9H); 2.48(s, 2H); 7.19(m, 1H); 7.44(m, 1H); 8.39(m, 1H );

8.45(m, 1H) δppm MS: 149(10, $M^{30}$ ), 134(10), 93(100), 65(8), 57(21)

What we claim is:

1. A method to impart, improve, enhance or modify the odor properties of a perfuming composition or of a perfumed article, which method comprises adding to said composition or article 3-(2,2-dimethyl-propyl)-pyridine in an amount effective to impart, enhance or modify the fragrance thereof.

2. A method to impart, improve, enhance or modify the odor properties of perfumes, colognes, skin or body-care products, cosmetic preparations, body deodorants or air fresheners, shampoos, hair-care products, soaps, detergents, fabric softeners or household products, which comprises adding thereto 3(2,2-dimethyl-propyl)-pyridine as a perfuming ingredient in an amount effective to impart, enhance, or modify the fragrance thereof.

3. A perfuming composition containing as active ingredient 3-(2,2-dimethyl-propyl)-pyridine.

4. A perfume, a cologne, a soap, a bath or shower gel, a shampoo or a hair conditioner, a cosmetic preparation, a body deodorant, an air freshener, a detergent or a fabric softener, or a household product containing as active perfuming ingredient 3-(2,2-dimethyl-propyl)-pyridine.

* * * * *